United States Patent
Bonacini

(10) Patent No.: US 8,221,506 B2
(45) Date of Patent: Jul. 17, 2012

(54) PROSTHETIC WALKING FOOT

(75) Inventor: Daniele Bonacini, Milan (IT)

(73) Assignee: Roadrunnerfoot Engineering S.R.L., Milan (IT)

( * ) Notice: Subject to any disclaimer, the term of this patent is extended or adjusted under 35 U.S.C. 154(b) by 95 days.

(21) Appl. No.: 12/364,814

(22) Filed: Feb. 3, 2009

(65) Prior Publication Data

US 2009/0204231 A1    Aug. 13, 2009

(30) Foreign Application Priority Data

Feb. 13, 2008  (IT) .............................. MI2008A0226

(51) Int. Cl.
    *A61F 2/66* (2006.01)
(52) U.S. Cl. ........................................... 623/52; 623/55
(58) Field of Classification Search ............... 623/47–56
    See application file for complete search history.

(56) References Cited

U.S. PATENT DOCUMENTS

| | | | | |
|---|---|---|---|---|
| 5,653,767 A | * | 8/1997 | Allen et al. ..................... | 623/52 |
| 5,653,768 A | * | 8/1997 | Kania .............................. | 623/55 |
| 5,944,760 A | * | 8/1999 | Christensen .................... | 623/55 |
| 6,241,776 B1 | * | 6/2001 | Christensen .................... | 623/52 |
| 6,942,704 B2 | * | 9/2005 | Sulprizio ........................ | 623/52 |
| 2002/0013628 A1 | * | 1/2002 | Harris ............................. | 623/55 |
| 2003/0191541 A1 | * | 10/2003 | Phillips .......................... | 623/55 |

* cited by examiner

*Primary Examiner* — William H Matthews
*Assistant Examiner* — Marcia Hoffman

(57) ABSTRACT

The prosthetic foot (1) consists of three or four laminas, a lower lamina (1*a*) defining the under-heel and the foot front, a rear lamina (1*b*) defining the heel and functioning as the Achilles tendon and as the soleus muscle, two upper laminas (1*c* and 1*d*) defining the front part of the foot and performing the function of the front tibial muscle, and a connector (2) in proximity to the ankle to serve as a coupling for a tube (3).

21 Claims, 3 Drawing Sheets

PROSTHETIC WALKING FOOT

FIELD OF THE INVENTION

The present invention relates to a prosthetic walking foot. In particular, the present invention relates to a prosthetic foot dedicated to lower limb-amputated subjects of considerable mobility and dynamicity, and hence normally dedicated to young or middle aged subjects.

BACKGROUND OF THE INVENTION

To satisfy the requirements of amputated persons of the 1980s, prosthetic feet providing energy return were launched on the market, these, by using composite materials such as carbon fibre, being able to store energy during the initial foot bearing phase, i.e. during so-called loading, and to return it during the subsequent ground support phase, known as the response, before take-off.

Typically, such prosthetic feet present an L-shaped lamina defining the front part of the foot, and a rear lamina defining the rear part or heel of the foot.

These prosthetic feet on the one hand provide good energy absorption during the initial part of the bearing state, hence ensuring good rear flexure of the foot, however they present minimal plantar flexure because of two factors:

in the final bearing phase, during toe-off, when ground contact takes place only via the tip of the foot front, the carbon fibre laminas of traditional prosthetic feet no longer function, i.e. no longer return energy, hence not enabling the user to make the final fundamental propulsive thrust;

the foot efficiency, i.e. the ratio of energy absorbed to energy returned by the prosthetic foot, is usually about 70%.

The technical aim of the present invention is therefore to provide a prosthetic foot which enables the stated technical drawbacks of the known art to be eliminated.

SUMMARY OF THE INVENTION

Within the scope of this technical aim, an object of the invention is to provide a prosthetic foot which simulates the functional behaviour of the human foot to a better extent than traditional prosthetic feet.

Another object of the invention is to provide a prosthetic foot which ensures good plantar flexure.

A further object of the invention is to provide a prosthetic foot which enables energy to be returned at every moment during ground bearing, and in particular during the final propulsive thrust, when the prosthetic foot is at toe-off.

A further object of the invention is to provide a prosthetic foot in which energy return is more effective than with commercially available feet.

The technical aim, together with these and further objects, are attained according to the present invention by a prosthetic foot in accordance with the accompanying claims.

Advantageously, the prosthetic foot of the invention must have sufficient strength to satisfy the ISO 10328 standard, while at the same time being flexible to enable the load to be applied and handled to produce smooth natural walking.

The foot of the new invention comprises four main laminas:

a lower, a rear and one or two upper laminas; they present profiles which are mostly curved and are connected together in pairs to ensure energy absorption and return by at least two laminas, for each phase of ground bearing during walking.

The lower lamina consists of:

an initial curved portion, connected in proximity to the natural under-heel, at the end of which an aperture or slot is present, the dimensions of which enable the rear lamina to pass through;

a curved or "humped" portion representative of the natural plantar arch, and with its vertex ($V_{linf}$) preferably passing through or in proximity to the loading straight line;

a straight connection portion;

a final portion defining the foot front.

The rear lamina consists of:

a straight portion enabling the laminas to be fixed (at the neck of the natural ankle) to a connector for a tube functionally reproducing the skeletal structure of a leg of a normal subject;

a curved portion defining the heel, with its centre of curvature ($C_{lpost}$) positioned at ⅓ of the length of the foot and having the functionality of Achilles tendons;

a connection portion between the two aforesaid portions;

a curved portion which passes through the lower lamina and terminates in proximity to the length of the prosthetic foot;

a curved final portion terminating at about the centre of the foot ($PC_{lpost}$), the length of the rear lamina being such that it enters into contact with the ground (via an aesthetic covering in the form of a human foot and a possible shoe) at mid-stance.

The one or two upper laminas have a similar profile and consist of:

a straight portion in proximity to the neck of the ankle, used for fixing the foot to the pyramidal connector;

a curved portion corresponding to the neck of the foot, terminating slightly before the foot front, at the position in which it is fixed to the lower lamina, and having its centre of curvature ($C_{lsup}$) positioned at ⅔ of the foot length and at a height corresponding to the commencement of the straight portion.

The connector connects the rear lamina to the upper lamina by a fixing, for example with nuts and bolts and, together with the upper laminas-lower lamina fixing, provides working continuity for the laminas and load transmission between the laminas during walking.

BRIEF DESCRIPTION OF THE DRAWINGS

Further characteristics and advantages of the invention will be more apparent from the description of a preferred but non-exclusive embodiment of the prosthetic foot according to the invention, illustrated by way of non-limiting example in the accompanying drawings, in which.

DETAILED DESCRIPTION

Figure 1:
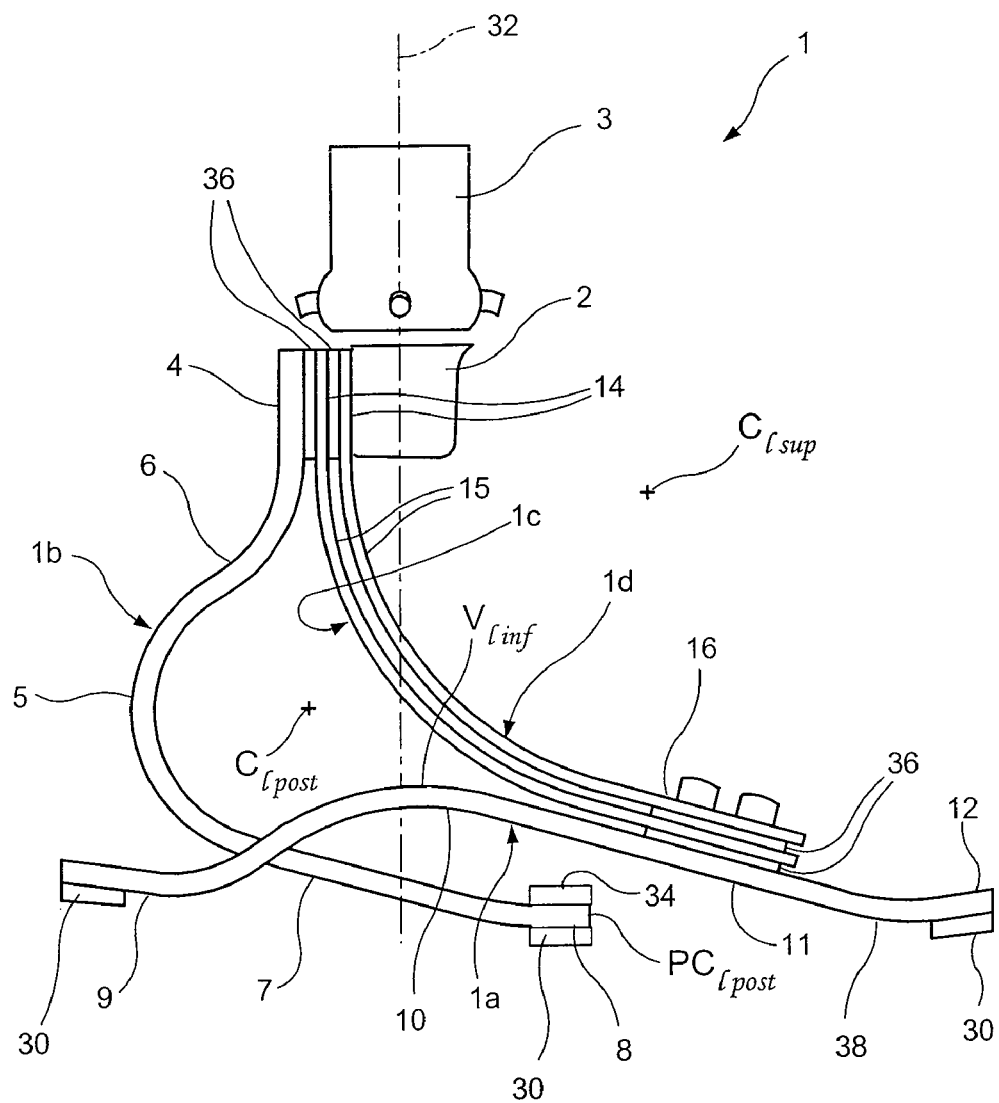
FIG. 1 is a side view of the prosthesis of the invention.
Figure 2:
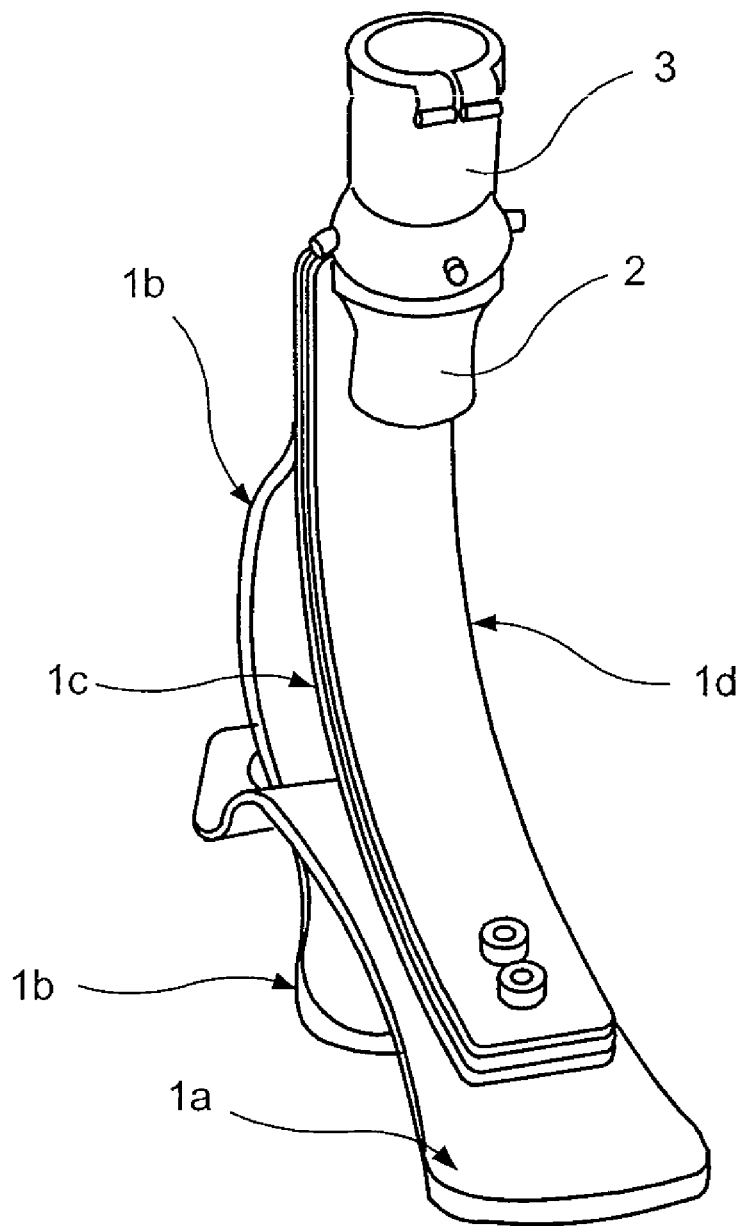
FIG. 2 is an isometric view of FIG. 1.
Figure 3:
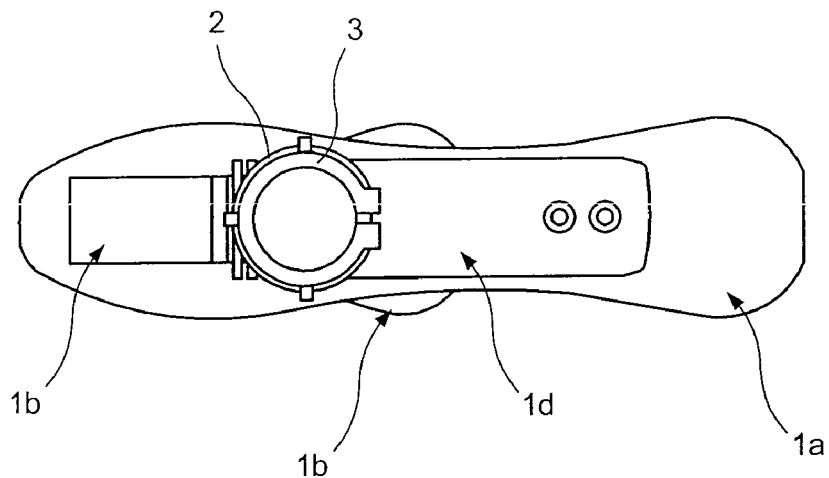
FIG. 3 is a view of the foot of FIG. 1 taken from above.
Figure 4:
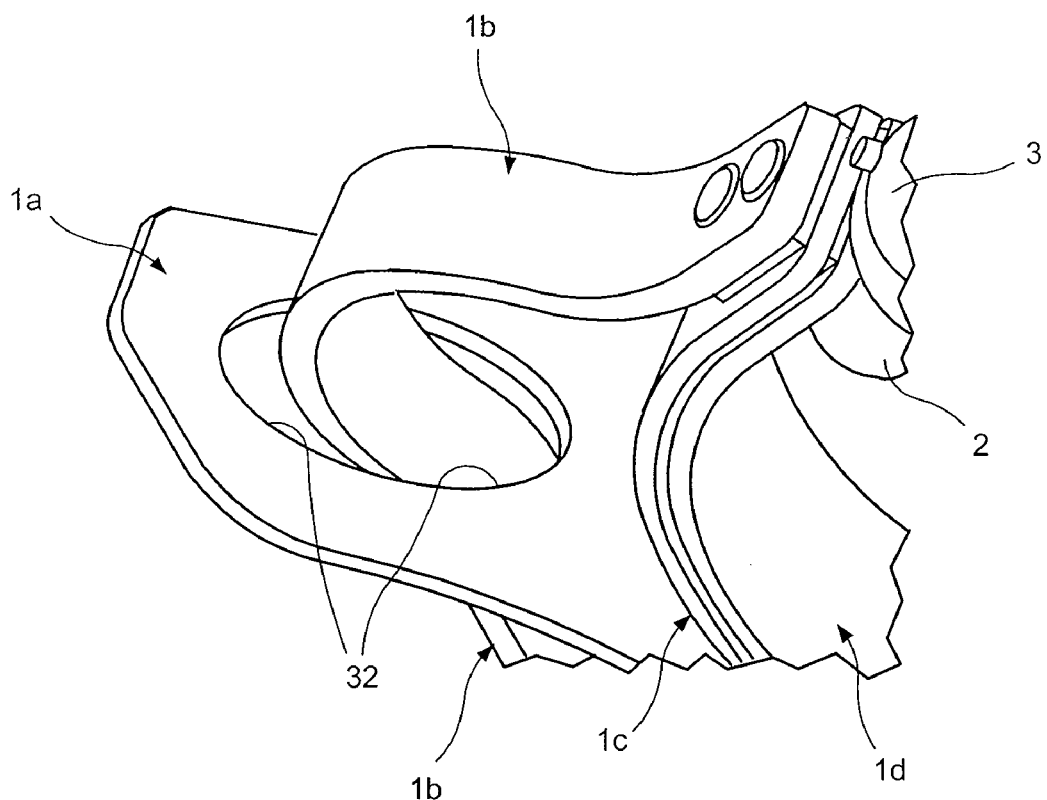
FIG. 4 shows a detail of a slot of a lower lamina of the foot of FIG. 1.

With reference to said figures, these show a prosthetic foot indicated overall by the reference numeral (1).

In the embodiment shown in the figures, the prosthetic foot (1) consists of four laminas: a lower lamina (1*a*), a rear lamina (1*b*) and two upper laminas (1*c* and 1*d*) positioned superposed, parallel and spaced apart.

The rear lamina 1b and the upper and lower laminas 1c and 1d are all fixed together at an upper end thereof to a pyramidal connector (2), which consists of a single piece of titanium or aluminium, by which the applied load is transferred to the prosthetic foot (1) by a tube (3).

The rear lamina (1b) consists of the following portions positioned in series: a straight first portion (4) in proximity to the connector (2) and to the neck of the virtual ankle, a curved second portion (5) with its concavity facing frontwards, positioned in proximity to the virtual heel and with centre of curvature ($C_{lpost}$), a third portion (6) connecting the first two together, a straight portion (7) and a curved final portion (8) terminating at about the centre of the foot ($PC_{lpost}$); this final portion (8) of the rear lamina (1b) is positioned below the humped portion (10) located between the initial portion (9) defining the under-heel and the final portion (12) defining the foot front of the lower lamina (1a).

The width of the cross-section of said lamina (1b), from the portion (4) to the portion (7), is constant (the cross-section is substantially rectangular), to increase after straddling the lower lamina (1a), until attaining the maximum width in the final portion (the cross-section is still substantially rectangular, but with its long sides of greater dimensions than the preceding cross-sections); at the portion (8) the lamina width is almost equal to the maximum width to the foot front, to ensure greater stability in mid-stance compared with traditional feet.

A 3 mm thick pad (30) of elastomeric material is positioned below the final portion of the rear lamina; this prevents direct contact between the lamina and the aesthetic polyurethane covering within which the prosthetic foot is housed during use.

The lower lamina (1a) consists of a curved portion (9) of upwardly facing concavity (when the foot is in its normal use configuration) and representing the under-heel, a curved humped portion (10) representing the plantar arch with its vertex ($V_{linf}$) located on a central axis (31) of the connector along which the user's weight is discharged, this axis (31) in practice being the loading straight line, and a straight portion (11) connecting the portion (10) to the final portion (12) defining the foot front, which presents an upward concavity and possibly an inflection.

The lower lamina (1a) and the upper lamina or laminas (1c and 1d) are connected together at a region of the lower lamina (1a) interposed between the initial portion (9) and the final portion (12).

In the portion (11) of the lower lamina (1a) two holes are present to enable it to be fixed to the two upper laminas by clamping with nuts and bolts.

The lower lamina (1a) presents an aperture or slot (32) through which the rear lamina (1b) passes.

The aperture or slot (32) is provided in the intermediate humped portion (10) of the lower lamina (1a).

In an alternative embodiment, the rear lamina (1b) presents an aperture through which the lower lamina (1a) passes.

Two pads (30) of elastomeric material are positioned below the portions (9) and (12) to prevent direct contact between the carbon fibre laminas and the aesthetic polyurethane covering within which the prosthetic foot is housed. These pads have a thickness of 3 mm. In addition, the rear lamina (1b) presents an elastomeric material pad (34) consisting of a 3 mm thick rubber block interposed between the top of its final portion (8) and the bottom of the lower lamina (1a), to prevent direct contact during loading, which could cause it to wear.

Aluminium spacers (36) are used in the fixing region at the ankle neck and at the foot front to prevent contact between the different laminas.

The overall length of the lower lamina (1a) is approximately equal to the length of a natural foot; it will evidently differ depending on the characteristics of each user and hence on the size of the prosthetic foot chosen on that basis.

The width of the cross-section of the lower lamina (1a) narrows from the portion (9) (which defines the heel) to the humped portion (10) (which defines the plantar arch), to then widen to reach its maximum value at the tip (38), which bounds the portions 11 and 12 of the lower lamina (1a) and is indicative of the $5^{th}$ virtual metatarsus, corresponding with the maximum width of the foot front.

Each of the upper laminas (1c and 1d) comprises the following portions in series: a straight portion (14) fixed to the connector (2) and positioned in proximity to the virtual ankle, a curved portion (15) with centre of curvature $C_{lpost}$ and a straight portion (16) in which two holes are present for fixing the two upper laminas (1c, 1d) to the lower lamina (1a).

The cross-section (and the section width) of these upper laminas (1c and 1d) remains constant for their entire length.

Advantageously, the use of two upper laminas achieves good elasticity characteristics associated with high strength, without the upper laminas being too rigid.

The lamina thicknesses are preferably constant for all laminas, being determined on the basis of the applied load and hence of the user is weight and mobility level. The connector is fixed to the front of the rear lamina (1b) and of the upper lamina or laminas (1c, 1d).

In addition, the axis (31) of this connector, which coincides with the force application axis when the prosthetic foot is worn, passes close to the vertex ($V_{linf}$) of the humped portion (10) of the lower lamina (1a).

The foot dimensions vary for the five classes according to the shoe size number of the user subject: class I No. 35-36, class II No. 37-38, class III No. 39-40, class IV No. 41-42, class V No. 43-44. Other classes are also possible.

The material with which this prosthetic foot is produced enables energy to be absorbed and released, it being a composite material such as carbon fibre fabric, aramid fibre fabric, glass fibre fabric, Kevlar and other fibre fabrics, impregnated with epoxy, acrylic or other resin.

Advantageously, the morphology of the prosthetic foot of the invention ensures that at least two laminas operate in each resting phase.

When in the dynamic condition, the weight is always discharged onto at least two laminas, which vary depending on the resting phase.

In this respect, during the initial contact phase, the lower lamina (1a) and the upper laminas (1c and 1d) work in synergy.

During mid-stance (when the two opposite ends of the lower lamina (1a) are in resting contact with the floor via the pads (30) and the aesthetic covering, of human foot form and possibly shoe form), the rear lamina (1b) and the upper laminas (1c and 1d) operate. During the final propulsive phase, in which only the foot front portion (12) of the lower lamina (1a) is in contact with the floor, the lower lamina (1a) and the upper laminas (1c and 1d) work in synergy.

In particular, during the initial contact phase, the portion (9) of the lower lamina (1a) (which defines the under-heel) ensures load acceptance and absorption and, by virtue of the two upper laminas (1c and 1d) secured to the lower lamina by fixings, performs the function of the front tibial muscle which ensures control of foot "rolling" and hence the heel contact with the ground until the foot front portion (12) of the lower lamina (1a) has completely contacted the ground.

From the moment when the portion (8) of the rear lamina (1b) comes into contact with the ground, the rear lamina (1b)

begins to load and to generate propulsive energy, facilitating passage from mid-stance to the final contact of the portion (12) of the lower lamina (1a) (which defines the foot front).

The rear lamina (1b) performs the function of the Achilles heel and hence of the soleus muscle which acts in eccentric contraction during the second rolling, to stabilize the resting of the foot in the sagittal plane.

The rear flexure of the prosthetic ankle which enables the portion (9) of the lower lamina (1a) (which defines the under-heel) to separate, and contact to pass to just the portion (12) of the lower lamina (1a) (which defines the foot front), is ensured by the flexure of the rear lamina and the two upper laminas.

In the final phase of ground resting, the two upper laminas (1c and 1d) release the energy stored in the previous phase, to facilitate the propulsive thrust of the portion (12) of the lower lamina (1a) (i.e. of the virtual foot front); this ensures effective toe-off and plantar flexure, in contrast to traditional feet which present a limited plantar flexure, of about 10°.

The shape and positioning of the laminas also ensure stability during the static phase with natural resting.

In this respect, under orthostatic conditions the weight is discharged onto the portion (9) of the lower lamina (1a) (which simulates the under-heel) and onto the portion (12) of said lower lamina (1a) (which simulates the foot front) and onto the portion (8) of the rear lamina (1b) (which simulates the intermediate bearing region).

In practice, the use of three or four laminas connected together enables the functionality of the human foot to be simulated and enables continuous absorption/return of energy by the foot such as to provide "completely assisted" walking by the prosthetic foot, at each moment of its resting on the ground. The prosthetic foot always operates via at least two laminas, of which one absorbs and the other returns energy. The device is arranged to be housed within an aesthetic covering having the shape of the human foot.

Numerous modifications and variants are possible.

Hence the two upper laminas 1c and 1d can be replaced by a single lamina or by more than two laminas, depending on the elasticity and strength characteristics required; thus one, two or even more upper laminas can be used, depending on the characteristics of the user.

Advantageously the foot presents a diagram of the vertical force discharged to the ground with the characteristic double humped pattern typical of the human foot, but presents a special characteristic which differentiates it therefrom and also from other traditional prosthetic feet: the first hump is lower during load acceptance, while the second hump is higher such that there is a greater propulsive thrust and a more effective plantar flexure than with traditional feet.

The invention claimed is:

1. A prosthetic walking foot comprising:
(a) a connector (2) that is fixable to a tube (3) of an artificial limb of a subject;
(b) at least one upper lamina (1c, 1d) extending from the connector and having a concavity facing in a forward direction;
(c) a lower lamina (1a) comprising an initial portion (9) defining an under-heel, an intermediate portion (10) comprising a hump and a final portion (12) defining a foot front, said lower lamina being joined to the at least one upper lamina solely in a region of the lower lamina disposed between said initial portion (9) and said final portion (12); and
(d) a rear lamina (1b) extending from the connector and comprising a curved region (5) having a concavity facing in the forward direction and an end portion (8) that is disposed under the hump of the intermediate portion of the lower lamina (1a), wherein the connector, the at least one upper lamina, the lower lamina and the rear lamina are constructed and arranged such that, in use, with the subject walking with the connector fixed to the tube of the artificial limb, the walking foot enters into contact with the ground at each of the following three points: the initial portion (9) of the lower lamina, the final portion (12) of the lower lamina and the end portion (8) of the rear lamina.

2. A prosthetic foot as claimed in claim 1, wherein said lower lamina presents an aperture or slot through which said rear lamina passes.

3. A prosthetic foot as claimed in claim 2, wherein said aperture is provided in said intermediate humped portion of said lower lamina.

4. A prosthetic foot as claimed in claim 1, wherein 1, said rear lamina presents an aperture through which said lower lamina passes.

5. A prosthetic foot as claimed in claim 1, wherein pads are positioned below the initial portion and final portion of the lower lamina and below the end portion of the rear lamina.

6. A prosthetic foot as claimed in claim 5, wherein two upper laminas.

7. A prosthetic foot as claimed in claim 1, wherein said at least one upper lamina comprises a straight first portion fixed to said connector, a curved intermediate portion, and a straight terminal portion, the curved intermediate portion having a center of curvature ($C_{1sup}$) positioned at ⅔ a length of the foot and at a height corresponding to a commencement of the straight portion.

8. A prosthetic foot as claimed in claim 1, wherein said initial portion and said final portion of said lower lamina are curved with their concavity facing upwards, said lower lamina also comprising straight portion interposed between said humped portion and said curved final portion, said lower lamina and said at least one upper lamina being joined at said straight portion of said lower lamina.

9. A prosthetic foot as claimed in claim 1, wherein said humped portion of said lower lamina has a vertex located on an axis of said connector along which the subject's weight is discharged.

10. A prosthetic foot as claimed in claim 1, wherein said final portion of said lower lamina is curved and has an inflection.

11. A prosthetic foot as claimed in claim 1, wherein said rear lamina presents in series: a straight first portion fixed to said connector, an intermediate curved portion with a center of curvature ($C_{1post}$), a straight portion and a final curved portion with concavity facing upwards and terminating at about a midpoint of the prosthetic foot, the straight portion of said rear lamina straddling said lower lamina.

12. A prosthetic foot as claimed in claim 1, comprising a pad of elastomeric material interposed between an upper face of the end portion of the rear lamina and a lower face of the lower lamina.

13. A prosthetic foot as claimed in claim 1, wherein said connector is fixed to a front of said rear lamina and of said at least one upper lamina.

14. A prosthetic foot as claimed in claim 1, wherein an axis of said connector, coinciding with a force application axis when said prosthetic foot is worn, passes in proximity to a vertex ($V_{linf}$) of said humped portion of said lower lamina.

15. A prosthetic foot as claimed in claim 1, wherein the rear lamina extends from the connector at the rear of the at least one upper lamina when considered from the forward direction, and said curved region has a center of curvature that is disposed under the at least one upper lamina with the rear lamina diverging away from the upper lamina in a portion of the curved region.

16. A prosthetic foot as claimed in claim 15, wherein the lower lamina is joined to an underside of the at least one upper lamina in said region of the lower lamina disposed between said initial portion (9) and said final portion (12) such that all portions of the lower lamina are disposed under the upper lamina.

17. A prosthetic foot as claimed in claim 1, wherein the lower lamina is joined to an underside of the at least one upper lamina in said region of the lower lamina disposed between said initial portion (9) and said final portion (12) such that all portions of the lower lamina are disposed under the upper lamina.

18. A prosthetic walking foot comprising:
a connector (2) that is fixable to a tube (3) of an artificial limb of a subject;
(b) at least one upper lamina (1c, 1d) extending from the connector and having a concavity facing in a forward direction;
(c) a lower lamina (1a) comprising an initial portion (9) defining an under-heel, an intermediate portion (10) comprising a hump and a final portion (12) defining a foot front, said lower lamina being joined to an underside of the at least one upper lamina in a region of the lower lamina disposed between said initial portion (9) and said final portion (12) such that all portions of the lower lamina are disposed under the upper lamina; and
(d) a rear lamina (1b) extending from the connector and comprising a curved region (5) having a concavity facing in the forward direction and an end portion (8) that is disposed under the hump of the intermediate portion of the lower lamina (1a), wherein the connector, the at least one upper lamina, the lower lamina and the rear lamina are constructed and arranged such that, in use, with the subject walking with the connector fixed to the tube of the artificial limb, the walking foot enters into contact with the ground at each of the following three points: the initial portion (9) of the lower lamina, the final portion (12) of the lower lamina and the end portion (8) of the rear lamina.

19. A prosthetic walking foot comprising:
(a) a connector (2) that is fixable to a tube (3) of an artificial limb of a subject;
(b) at least one upper lamina (1c, 1d) extending from the connector and having a concavity facing in a forward direction;
(c) a lower lamina (1a) comprising an initial portion (9) defining an under-heel, an intermediate portion (10) comprising a hump and a final portion (12) defining a foot front, said lower lamina being joined to the at least one upper lamina in a region of the lower lamina disposed between, said initial portion (9) and said final portion (12); and
(d) a rear lamina (1b) extending from the connector at the rear of the at least one upper lamina when considered from the forward direction and comprising a curved region (5) having a concavity facing in the forward direction and an end portion (8) that is disposed under the hump of the intermediate portion of the lower lamina (1a), said curved region having a center of curvature that is disposed under the at least one upper lamina with the rear lamina diverging away from the upper lamina in a portion of the curved region, wherein the connector, the at least one upper lamina, the lower lamina and the rear lamina are constructed and arranged such that, in use, with the subject walking with the connector fixed to the tube of the artificial limb, the walking foot enters into contact with the ground at each of the following three points: the initial portion (9) of the lower lamina, the final portion (12) of the lower lamina and the end portion (8) of the rear lamina.

20. A prosthetic foot as claimed in claim 19, wherein the lower lamina is joined to the at least one upper lamina solely in the region of the lower lamina disposed between said initial portion and said final portion.

21. A prosthetic foot as claimed in claim 20, wherein the rear lamina passes through a slot in the lower lamina or the lower lamina passes through a slot in the rear lamina.

* * * * *